United States Patent [19]

Tsujihara et al.

[11] 4,241,053
[45] Dec. 23, 1980

[54] NOVEL NITROSOUREA COMPOUNDS AND PROCESS FOR PREPARING THE SAME

[75] Inventors: Kenji Tsujihara, Urawa; Masakatsu Ozeki, Wako; Yoshihisa Arai, Urawa, all of Japan

[73] Assignee: Tanabe Seiyaku Co., Ltd., Osaka, Japan

[21] Appl. No.: 66,421

[22] Filed: Aug. 14, 1979

[30] Foreign Application Priority Data

Aug. 25, 1978 [GB] United Kingdom ............... 34564/78
Jan. 27, 1979 [GB] United Kingdom ............... 02957/79

[51] Int. Cl.³ .................... A61K 31/70; A61K 31/73; C07H 13/12
[52] U.S. Cl. ...................... 424/180; 536/18; 536/22; 536/53
[58] Field of Search .................... 424/180; 536/53, 22, 536/18

[56] References Cited

U.S. PATENT DOCUMENTS

| | | | |
|---|---|---|---|
| 3,577,406 | 5/1971 | Hessler | 536/53 |
| 4,086,415 | 4/1978 | Suami et al. | 536/53 |
| 4,156,777 | 5/1979 | Kimura | 536/53 |
| 4,157,439 | 6/1979 | Suami et al. | 536/53 |

*Primary Examiner*—Johnnie R. Brown
*Attorney, Agent, or Firm*—Bierman & Bierman

[57] ABSTRACT

A compound of the formula:

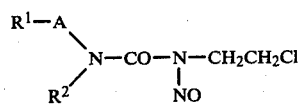

wherein $R^1$ is lower alkoxy, lower alkoxy-methoxy or 2-hydroxy-ethoxy, $R^2$ is aldo-pentofuranosyl, aldo-pentopyranosyl, aldohexopyranosyl or O-aldo-hexopyranosyl-(1→4)-aldo-hexopyranosyl, and A is straight or branched alkylene of one to four carbon atoms, said alkylene being substituted with from 0 to at least one lower alkoxy group, is disclosed. A new intermediate used in the preparation of this compound is also disclosed. The end products are useful for inhibiting the growth of malignant tumor cells in warm-blooded animals; especially Leukemia and Ejrlich ascites carcinoma. Effectiveness on human beings has not yet been demonstrated.

20 Claims, No Drawings

NOVEL NITROSOUREA COMPOUNDS AND PROCESS FOR PREPARING THE SAME

This invention relates to a novel nitrosourea compound and a process for preparing the same. More particularly, it relates to a compound of the formula:

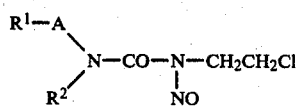

wherein $R^1$ is lower alkoxy, lower alkoxy-methoxy or 2-hydroxyethoxy, $R^2$ is aldo-pentofuranosyl, aldo-pentopyranosyl, aldohexopyranosyl or O-aldo-hexopyranosyl-(1→4)-aldo-hexopyranosyl, and A is straight or branched alkylene of one to four carbon atoms (said alkylene being optionally substituted with lower alkoxy).

It is known that (N'-chloroethyl-N'-nitrosocarbamoyl)-amino derivatives of monosaccharides are prepared by nitrosation of (N'-chloroethylcarbamoyl)amino-monosaccharides with an alkali metal nitrite such as sodium nitrite (U.S. Pat. No. 4086451 and Japanese Patent Publication (unexamined) Nos. 108043/1976 and 52128/1976). These patents also disclose that 1-(2-chloroethyl)-1-nitroso-3-(D-mannopyranosyl)urea and 1-(2-chloroethyl)-1-nitroso-3-(D-glucopyranosyl)urea (The latter compound being hereinafter referred to as "GANU") increase the life span of mice implanted intraperitoneally with the tumor cells of lymphoid leukemia L-1210. Further, it is known that (N'-chloroethyl-N'-nitrosocarbamoyl)amino derivatives of disaccharides such as 1-(2-chloroethyl)-1-nitroso-3-(D-lactosyl)urea and 1-(2-chloroethyl)-1-nitroso-3-(D-maltosyl)urea are prepared from the corresponding (N'-chloroethylcarbamoyl)amino-disaccharides in the same manner as above and show anti-tumor activity against leukemic cells (Japanese Patent Publication (unexamined) No. 141815/1976).

We have now found that the nitrosourea compound [I] of the present invention shows potent anti-tumor or anti-leukemic activity and is useful to inhibit the growth of malignant tumor cells in warm-blooded animals. For example, when the anti-tumor effects upon leukemia is estimated by administering such drugs intraperitoneally to tumor cell-inoculated mice (i.e., mice implanted with tumor cells of Leukemia L-1210) for five consecutive days, 1-(2-chloroethyl)-1-nitroso-3-(2-methoxy-n-propyl)-3-(L-arabinopyranosyl)urea at the daily dose of 0.5 mg/kg or 1-(2-chloroethyl)-1-nitroso-3-(1-methyl-2-methoxy-ethyl)-3-(L-arabinopyranosyl)urea at the daily dose of 0.45 mg/kg shows an increase of about 30% in the average life span of said mice. Moreover, the nitrosourea compound [I] of the present invention is characterized by its great safety for use as an anti-tumor agent. For example, when the therapeutic index is estimated by the ratio of the optimal dose (the daily dose at which the maximum increase in the life span of tumor cell-inoculated mice occurs) to $ILS_{30}$ (the minimum daily dose which shows an increase of 30% in the life span of said mice) in case of Leukemia L-1210, said therapeutic indexes of 1-(2-chloroethyl)-1-nitroso-3-(1-methyl-2-methoxy-ethyl)-3-[O-α-D-glucopyranosyl-(1→4)-D-glucopyranosyl]urea, 1-(2-chloroethyl)-1-nitroso-3-(3-methoxy-n-propyl)-3-(L-arabinopyranosyl)urea and 1-(2-chloroethyl)-1-nitroso-3-(3-methoxy-n-propyl)-3-(D-arabinopyranosyl)urea may be about 7 to 12 times greater than that of GANU. The compound [I] may also show an excellent therapeutic index estimated in terms of ratio of M.T.D. (the maximum tolerated dose which shows 100% inhibition for the growth of Ehrlich ascites tumor in mice without causing the death of said mice) to M.E.D. (the minimum effective dose which shows 100% inhibition for the growth of said ascites tumor). For example, said therapeutic indexes (M.T.D./M.E.D.) of 1-(2-chloroethyl)-1-nitroso-3-(1-methyl-2-methoxy-ethyl)-3-[O-α-D-glucopyranosyl-(1→4)-D-glucopyranosyl]-urea, 1-(2-chloroethyl)-1-nitroso-3-(3-methoxy-n-propyl)-3-(L-arabinopyranosyl)urea and 1-(2-chloroethyl)-1-nitroso-3-(3-methoxy-n-propyl)-3-(D-arabinopyranosyl)urea are 4 times greater than that of GANU.

In the above-mentioned formula [I], representative examples of the group $R^1$ include lower alkoxy such as methoxy, ethoxy and propoxy; lower alkoxy-methoxy such as methoxymethoxy and ethoxymethoxy; and 2-hydroxyethoxy. On the other hand, representative examples of the group $R^2$ include aldo-pentofuranosyl such as D-ribofuranosyl and D-deoxyribofuranosyl; aldo-pentopyranosyl such as L-arabinopyranosyl, D-arabinopyranosyl and D-xylopyranosyl; aldo-hexopyranosyl such as D-glucopyranosyl, D-galactopyranosyl, D-mannopyranosyl, L-rhamnopyranosyl, D-fucopyranosyl and D-talopyranosyl; and O-aldo-hexopyranosyl-(1→4)-aldo-hexopyranosyl such as O-α-D-glucopyranosyl-(1→4)-D-glucopyranosyl (=D-maltosyl) and O-β-D-galactopyranosyl-(1→4)-D-glucopyranosyl (=D-lactosyl). Further, representative examples of the group A include straight or branched alkylene such as methylene, ethylene, propylene, butylene, 1-methylethylene, 1-ethylethylene, 2-methylethylene and 2-ethylethylene; and lower alkoxy-substituted alkylene such as 2-methoxyethylene, 2-ethoxyethylene, 2-methoxypropylene and 2-ethoxypropylene. Among those of the invention, a preferred subgenus includes the compound of the formula [I] in which $R^2$ is D-ribofuranosyl, L-arabinopyranosyl, D-arabinopyranosyl, D-xylopyranosyl, D-glucopyranosyl, D-galactopyranosyl, D-mannopyranosyl or O-α-D-glucopyranosyl-(1→4)-D-glucopyranosyl. Another preferred subgenus includes the compound of the formula [I] in which $R^1$ is alkoxy of one or two carbon atoms, $R^2$ is D-ribofuranosyl, L-arabinopyranosyl, D-arabinopyranosyl, D-xylopyranosyl, D-galactopyranosyl, D-mannopyranosyl or O-α-D-glucopyranosyl-(1→4)-D-glucopyranosyl, and A is straight or branched alkylene of two or three carbon atoms. A further preferred subgenus includes the compound of the formula [I] in which $R^1$ is alkoxy of one or two carbon atoms, $R^2$ is L-arabinopyranosyl, D-arabinopyranosyl or O-α-D-glucopyranosyl-(1→4)-D-glucopyranosyl, and A is ethylene, propylene, 1-methylethylene or 2-methylethylene.

According to the present invention, the nitrosourea compound [I] is prepared by nitrosation of a compound of the formula:

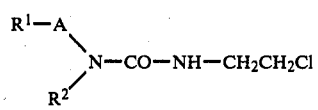

wherein $R^1$, $R^2$ and A are the same as defined above.

The starting compound [II] is readily obtained. For example, it can be prepared by condensing a primary amine of the formula: $R^1-A-NH_2$ (wherein $R^1$ and A are the same as defined above) with a compound of the formula: $R^2-OH$ (wherein $R^2$ is the same as defined above) at about 20° to 80° C. in an inert solvent (e.g., methanol, ethanol) to give a secondary amine of the formula:

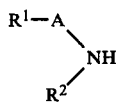

(wherein $R^1$, $R^2$ and A are the same as defined above), and then condensing said secondary amine with 2-chloroethyl isocyanate at 0° to 30° C. in an inert solvent (e.g., tetrahydrofuran, methanol, ethanol).

The nitrosation of the invention is accomplished by contacting the compound [II] with nitrous acid, nitrogen trioxide or nitrogen tetroxide in an inert solvent. The reaction can be preferably carried out at a temperature of $-20°$ to 20° C., especially at about 0° to about 5° C. Water, lower alkanols (e.g., methanol, ethanol), tetrahydrofuran, methylene chloride, ethyl acetate, acetic acid, and formic acid are suitable examples of the inert solvents. When free nitrous acid is prepared by reacting an alkali metal salt of nitrous acid (e.g., sodium nitrite, potassium nitrite) or a lower alkyl ester thereof (e.g., butyl nitrite, amyl nitrite) with a mineral or organic acid (e.g., hydrochloric acid, sulfuric acid, formic acid or acetic acid), it is preferred that said free nitrous acid is employed for subsequent nitrosation reaction immediately after preparation thereof. On the other hand, when nitrogen trioxide or nitrogen tetroxide is employed in the invention, it is preferred to carry out the nitrosation reaction by dissolving or suspending the starting compound [II] in the inert solvent and then introducing gaseous nitrogen trioxide or tetroxide thereto in the presence or absence of an acid acceptor. Sodium bicarbonate, sodium carbonate, potassium carbonate, sodium acetate, potassium acetate are examples of suitable acid acceptors. When the nitrosation reaction is completed, the compound [I] of the invention is readily recovered from the reaction mixture and may be, if required, further purified by silica gel chromatography.

The nitrosourea compound [I] thus obtained shows potent anti-tumor activity against various tumor cells such as Ehrlich's carcinoma, Sarcoma 180, Leukemia L-121:, Lewis lung carcinoma, Yoshida sarcoma and Rat ascites hepatoma. It may be useful to prolong the survival time of warm-blooded animals afflicted with said tumors and/or minimize the growth of said tumors in said animals. It may also be employed for therapy of malignant lymphoma, leukemia, stomach tumor and hepatoma in test animals. Effectiveness in human beings has not yet been demonstrated. The nitrosourea compound [I] can be used for pharmaceutical use in the form of a pharmaceutical preparation suitable for either oral or parenteral administration. The compound [I] may also be used in conjunction or admixture with a pharmaceutical excipient. The excipient selected must be the one which does not react with the compound [I]. Suitable excipients include, for example, gelatin, lactose, glucose, sodium chloride, starch, magnesium stearate, talcum, vegetable oil and so forth. Other known medicinal excipients may be employed. The pharmaceutical preparation may be a solid dosage form such as, for example, a tablet, a coated tablet, a pill or a capsule; or a liquid dosage form such as, for example, a solution, a suspension or an emulsion. Further, the compound [I] may be employed, for example, in the form of an injection or suppository when administered parenterally. The pharmaceutical preparation may be sterilized and/or may contain auxiliaries such as, for example, preserving and stabilizing agents. The dose of the compound [I] for pharmaceutical use depends on route of administration; the age, weight and condition; and particular diseases to be treated. In general, it may be used for pharmaceutical use at a dose of 0.1 to 30 mg/kg, especially 0.2 to 10 mg/kg, per day.

Experiments

Chemotherapeutic effects of the nitrosourea compounds of the invention on a variety of tumor cells in mice were investigated by the following methods and materials.

[METHODS]

(A) Preventive effect against the growth of Ehrlich ascites tumor:

$10^6$ tumor cells of Ehrlich ascites carcinoma were inoculated intraperitoneally into a group of five femal mice (ICR mice, body weight: 19–23 g). A test compound was dissolved in a physiological saline solution [In the case where CCNU was employed as the test compound, said compound was suspended in a physiological saline solution containing 0.1% NIKKOL HCO-60 (trademark; a surface active agent manufactured by Nikko Chemicals Co. Ltd.)] and administered intraperitoneally to the mice. The administration of the test compound was begun 24 hours after the inoculation of the tumor cells and performed once a day for 5 days. The volume of ascites in the treated mice were measured after 7 days of the experiment.

(B) Effect on the life span of mice implanted with leukemic cells of L-1210:

$10^5$ leukemic cells of L-1210 were inoculated intraperitoneally into a group of four or six male mice (BDF$_1$ mice, body weight: 19–23 g). A test compound was dissolved in a physiological saline solution and administered intraperitoneally to the mice. The administration of the test compound was begun 24 hours after the inoculation of the leukemic cells and performed once a day for 5 days. The survival days of the treated mice were observed.

[COMPOUNDS TESTED]

Compound Nos. Chemical Names (The compounds of the present invention)

1. 1-(2-chloroethyl)-1-nitroso-3-(2-methoxy-n-propyl)-3-[O-α-D-glucopyranosyl-(1→4)-D-glucopyranosyl]urea
2. 1-(2-chloroethyl)-1-nitroso-3-(1-methyl-2-methoxyethyl)-3-[O-α-D-glucopyranosyl-(1→4)-D-glucopyranosyl]urea
3. 1-(2-chloroethyl)-1-nitroso-3-(2-methoxyethyl)-3-(L-arabinopyranosyl)urea
4. 1-(2-chloroethyl)-1-nitroso-3-(3-methoxy-n-propyl)-3-(L-arabinopyranosyl)urea
5. 1-(2-chloroethyl)-1-nitroso-3-(2-methoxy-n-propyl)-3-(L-arabinopyranosyl)urea 6. 1-(2-chloroethyl)-1-nitroso-3-(1-methyl-2-methoxyethyl)-3-(L-arabinopyranosyl)urea
7. 1-(2-chloroethyl)-1-nitroso-3-(3-methoxy-n-propyl)-3-(D-arabinopyranosyl)urea
8. 1-(2-chloroethyl)-1-nitroso-3-(1-methyl-2-methoxyethyl)-3-(D-galactopyranosyl)urea
9. 1-(2-chloroethyl)-1-nitroso-3-(2-methoxyethyl)-3-(D-ribofuranosyl)urea
10. 1-(2-chloroethyl)-1-nitroso-3-(2-methoxyethyl)-3-(D-xylopyranosyl)urea
11. 1-(2-chloroethyl)-1-nitroso-3-(2-methoxyethyl)-3-(D-mannopyranosyl)urea
12. 1-(2-chloroethyl)-1-nitroso-3-(3-methoxy-n-propyl)-3-(D-glucopyranosyl)urea (Known compounds)

CCNU: 1-(2-chloroethyl)-1-nitroso-3-cyclohexylurea
GANU: 1-(2-chloroethyl)-1-nitroso-3-(D-glucopyranosyl)urea

[RESULTS]

The results of the experiments are shown in the following Tables 1 and 2.

TABLE 1

Preventive effect against the growth of Ehrlich ascites carcinoma (Method A)

| Compound Nos. | Dose (mg kg/day) | Ascites volume(g) T/C[a] | Inhibition ratio[b] (%) | MTD[c] | MED[d] | Therapeutic index[e] |
|---|---|---|---|---|---|---|
| 1. | 400 | — | Toxic(4/5)* | 200 | 3.12 | 64 |
|  | 200 | 0.0/4.5 | 100 |  |  |  |
|  | 50 | 0.0/4.5 | 100 |  |  |  |
|  | 12.5 | 0.0/4.5 | 100 |  |  |  |
|  | 3.12 | 0.0/4.5 | 100 |  |  |  |
|  | 1.56 | 4.3/4.5 | 4.4 |  |  |  |
| 2. | 400 | — | Toxic(2/5)* | 200 | 1.56 | 128 |
|  | 200 | 0.0/3.5 | 100 |  |  |  |
|  | 50 | 0.0/3.5 | 100 |  |  |  |
|  | 12.5 | 0.0/3.5 | 100 |  |  |  |
|  | 3.12 | 0.0/3.5 | 100 |  |  |  |
|  | 1.56 | 0.0/3.5 | 100 |  |  |  |
|  | 0.78 | 3.8/3.5 | −8.6 |  |  |  |
| 3. | 100 | — | Toxic(3/5)* | 50 | 0.39 | 128 |
|  | 50 | 0.0/4.5 | 100 |  |  |  |
|  | 12.5 | 0.0/4.5 | 100 |  |  |  |
|  | 3.12 | 0.0/4.5 | 100 |  |  |  |
|  | 0.78 | 0.0/4.5 | 100 |  |  |  |
|  | 0.39 | 0.0/4.5 | 100 |  |  |  |
|  | 0.19 | 2.0/4.5 | 55.6 |  |  |  |
|  | 0.09 | 3.9/4.5 | 13.5 |  |  |  |
| 4. | 100 | — | Toxic(2/5)* | 50 | 0.39 | 128 |
|  | 50 | 0.0/4.9 | 100 |  |  |  |
|  | 12.5 | 0.0/4.9 | 100 |  |  |  |
|  | 3.12 | 0.0/4.9 | 100 |  |  |  |
|  | 0.78 | 0.0/4.9 | 100 |  |  |  |
|  | 0.39 | 0.0/4.9 | 100 |  |  |  |
|  | 0.19 | 2.7/4.9 | 44.9 |  |  |  |
|  | 0.09 | 4.0/4.9 | 18.4 |  |  |  |
| 5. | 100 | — | Toxic(4/5)* | 50 | 0.39 | 128 |
|  | 50 | 0.0/4.9 | 100 |  |  |  |
|  | 12.5 | 0.0/4.9 | 100 |  |  |  |
|  | 3.12 | 0.0/4.9 | 100 |  |  |  |
|  | 0.78 | 0.0/4.9 | 100 |  |  |  |
|  | 0.39 | 0.0/4.9 | 100 |  |  |  |
|  | 0.19 | 3.1/4.9 | 36.7 |  |  |  |
|  | 0.09 | 4.5/4.9 | 8.2 |  |  |  |
| 6. | 100 | — | Toxic(5/5)* | 50 | 0.78 | 64 |
|  | 50 | 0.0/3.8 | 100 |  |  |  |
|  | 12.5 | 0.0/3.8 | 100 |  |  |  |
|  | 3.12 | 0.0/3.8 | 100 |  |  |  |
|  | 0.78 | 0.0/3.8 | 100 |  |  |  |
|  | 0.39 | 0.3/3.8 | 92.1 |  |  |  |
|  | 0.19 | 1.4/3.8 | 63.2 |  |  |  |
|  | 0.09 | 3.2/3.8 | 15.8 |  |  |  |
| 7. | 200 | — | Toxic(5/5)* | 100 | 0.78 | 128 |
|  | 100 | 0.0/5.6 | 100 |  |  |  |
|  | 25 | 0.0/5.6 | 100 |  |  |  |
|  | 6.25 | 0.0/5.6 | 100 |  |  |  |
|  | 1.56 | 0.0/5.6 | 100 |  |  |  |
|  | 0.78 | 0.0/5.6 | 100 |  |  |  |
|  | 0.39 | 1.5/5.6 | 73.2 |  |  |  |
|  | 0.19 | 4.3/5.6 | 23.2 |  |  |  |
| 8. | 200 | — | Toxic(5/5)* | 100 | 1.56 | 64 |
|  | 100 | 0.0/3.8 | 100 |  |  |  |
|  | 25 | 0.0/3.8 | 100 |  |  |  |
|  | 6.25 | 0.0/3.8 | 100 |  |  |  |
|  | 1.56 | 0.0/3.8 | 100 |  |  |  |
|  | 0.78 | 1.3/3.8 | 65.8 |  |  |  |
|  | 0.39 | 3.1/3.8 | 18.4 |  |  |  |
| 9. | 100 | — | Toxic(3/5)* | 50 | 0.78 | 64 |
|  | 50 | 0.0/5.0 | 100 |  |  |  |
|  | 12.5 | 0.0/5.0 | 100 |  |  |  |
|  | 3.12 | 0.0/5.0 | 100 |  |  |  |
|  | 0.78 | 0.0/5.0 | 100 |  |  |  |
|  | 0.39 | 1.9/5.0 | 62.0 |  |  |  |
|  | 0.19 | 4.0/5.0 | 20.0 |  |  |  |
| 10. | 50 | — | Toxic(2/5)* | 25 | 0.39 | 64 |
|  | 25 | 0.0/4.8 | 100 |  |  |  |
|  | 6.23 | 0.0/4.8 | 100 |  |  |  |
|  | 1.56 | 0.0/4.8 | 100 |  |  |  |
|  | 0.39 | 0.0/4.8 | 100 |  |  |  |
|  | 0.19 | 0.5/4.8 | 89.6 |  |  |  |
|  | 0.09 | 3.6/4.8 | 25.0 |  |  |  |
|  | 0.04 | 4.7/4.8 | 2.1 |  |  |  |
| 11. | 800 | — | Toxic(5/5)* | 400 | 6.25 | 64 |
|  | 400 | 0.0/5.0 | 100 |  |  |  |
|  | 100 | 0.0/5.0 | 100 |  |  |  |
|  | 25 | 0.0/5.0 | 100 |  |  |  |
|  | 6.25 | 0.0/5.0 | 100 |  |  |  |
|  | 3.12 | 1.8/5.0 | 64.0 |  |  |  |
|  | 1.56 | 4.3/5.0 | 14.0 |  |  |  |
| 12. | 200 | — | Toxic(5/5)* | 100 | 3.12 | 32 |
|  | 100 | 0.0/5.0 | 100 |  |  |  |
|  | 25 | 0.0/5.0 | 100 |  |  |  |
|  | 6.25 | 0.0/5.0 | 100 |  |  |  |
|  | 3.12 | 0.0/5.0 | 100 |  |  |  |
|  | 1.56 | 0.5/5.0 | 90.0 |  |  |  |
|  | 0.78 | 3.3/5.0 | 34.0 |  |  |  |
|  | 0.39 | 4.5/5.0 | 10.0 |  |  |  |
| CCNU | 100 | — | Toxic(5/5)* | 50 | 12.5 | 4 |
|  | 50 | 0.0/5.7 | 100 |  |  |  |
|  | 12.5 | 0.0/5.7 | 100 |  |  |  |
|  | 6.25 | 3.8/5.7 | 33.3 |  |  |  |
|  | 3.12 | 4.5/5.7 | 21.1 |  |  |  |
| GANU | 25 | — | Toxic(5/5)* | 12.5 | 0.39 | 32 |
|  | 1.25 | 0.0/4.8 | 100 |  |  |  |
|  | 3.12 | 0.0/4.8 | 100 |  |  |  |
|  | 0.78 | 0.0/4.8 | 100 |  |  |  |
|  | 0.39 | 0.0/4.8 | 100 |  |  |  |
|  | 0.19 | 1.0/4.8 | 79.2 |  |  |  |
|  | 0.09 | 4.6/4.8 | 4.2 |  |  |  |

Note:
[a] T = the average volume of ascites in the treated mice
C = the average volume of ascites in the untreated mice (control group of mice)

[b] Inhibition ratio (%) = $\frac{C - T}{C} \times 100$

[c] MTD = Maximum Tolerated Dose (i.e., the maximum dose which shows 100% inhibition for the growth of Ehrlich ascites tumor in mice without causing the death of said mice)

[d] MED = Minimum Effective Dose (i.e., the minimum dose which shows 100% inhibition for the growth of said ascites tumor)

[e] Therapeutic index = MTD/MED

*the number of mice died/the number of mice used

TABLE 2

Effect on life span of mice implanted with Leukemia L-1210 (Method B)

| Compound Nos. | Dose (mg/kg/day) | Mean survival days (T/C)[a] | ILS[b] (%) | 60-day survivors[c] |
|---|---|---|---|---|
|  | 100 | >60.0/7.0 | >757.1 | 4/4 |
|  | 50 | >60.0/7.0 | >757.1 | 4/4 |
| 2. | 25 | >49.3/7.0 | >604.3 | 3/4 |
|  | 6.25 | 13.0/7.0 | 85.7 | 0/4 |
|  | 50 | >51.5/7.2 | >615.3 | 5/6 |
|  | 25 | >60.0/7.2 | >733.3 | 6/6 |
| 3. | 12.5 | >47.2/7.2 | >555.6 | 4/6 |
|  | 6.25 | 13.5/7.2 | 87.5 | 0/6 |
|  | 50 | >60.0/7.2 | >733.3 | 6/6 |
|  | 25 | >60.0/7.2 | >733.3 | 6/6 |
| 4. | 12.5 | >30.5/7.2 | >323.6 | 2/6 |
|  | 6.25 | 14.2/7.2 | 97.2 | 0/6 |
|  | 50 | >56.0/7.2 | >677.8 | 3/4 |
|  | 25 | >60.0/7.2 | >733.3 | 4/4 |
| 5. | 12.5 | >45.3/7.2 | >529.2 | 3/4 |
|  | 6.25 | 13.8/7.2 | 91.7 | 0/4 |
|  | 25 | >60.0/7.3 | >721.9 | 4/4 |
|  | 12.5 | >60.0/7.3 | >721.9 | 4/4 |
| 6. | 6.25 | >27.0/7.3 | >269.9 | 1.4 |
|  | 1.56 | 11.5/7.3 | 57.5 | 0/4 |
|  | 50 | >60.0/8.1 | >640.7 | 4/4 |
|  | 25 | >60.0/8.1 | >640.7 | 4/4 |
| 7. | 12.5 | >25.5/8.1 | >214.8 | 1/4 |
|  | 3.12 | 13.5/8.1 | 66.7 | 0/4 |
|  | 50 | >60.0/7.3 | >721.9 | 4/4 |
| 8. | 25 | >43.5/7.3 | >495.9 | 2/4 |
|  | 12.5 | 18.8/7.3 | 157.5 | 0/4 |
|  | 50 | >60.0/7.0 | >757.1 | 4/4 |
|  | 25 | >60.0/7.0 | >757.1 | 4/4 |
| 9. | 12.5 | >36.0/7.0 | >414.3 | 2/4 |
|  | 6.25 | >24.0/7.0 | >242.9 | 1/4 |
|  | 1.56 | 9.8/7.0 | 40.0 | 0/4 |
|  | 50 | >60.0/7.0 | >757.1 | 4/4 |
| 12. | 25 | >28.3/7.0 | >304.3 | 1/4 |
|  | 12.5 | 17.5/7.0 | 150..0 | 0/4 |

Note:
[a]T = the mean survival days of the treated mice
C = the mean survival days of the untreated mice (control group of mice)
[b]ILS(Increase in Life Span) = $\frac{T-C}{C} \times 100$
[c]60-day survivors = the number of mice survived for 60 days/the number of mice used Practical and presently-preferred embodiments of the present invention are illustratively shown in the following Examples. Through the specification and claims, the term "lower alkoxy" should be interpreted as referring to an alkoxy group having one to four carbon atoms.

EXAMPLE 1

(1) A mixture of 7.2 g of D-maltose monohydrate, 2.3 g of 2-methoxyethylamine and 15 ml of methanol are heated at 60° to 65° C. for 40 minutes under stirring. The reaction mixture is condensed to dryness under reduced pressure. The residue is washed with ether, whereby 1-(2-methoxyethylamino)-1-deoxy-D-maltose is obtained as a crude product. Said crude product is dissolved in 50 ml of methanol, and a solution of 2.5 g of 2-chloroethyl isocyanate in 10 ml of tetrahydrofuran is added dropwise thereto at 0° to 5° C. Said mixture is stirred at room temperature for one hour. After the reaction, the mixture is condensed under reduced pressure. The residue thus obtained is washed with ether, whereby 8.5 g of 1-(2-chloroethyl)-3-(2-methoxyethyl)-3-[O-α-D-glucopyranosyl-(1→4)-D-glucopyranosyl]urea (i.e., 1-(2-chloroethyl)-3-(2-methoxyethyl)-3-(D-maltosyl)urea) are obtained as colorless powder.

IR$\nu_{max}^{Nujol}$(cm$^{-1}$): 3350, 1630, 1540, 1070, 1025
NMR(D$_2$O)δ: 3.35(s, OC$\underline{H}_3$)

(2) 5.0 g of 1-(2-chloroethyl)-3-(2-methoxyethyl)-3-[O-α-D-glucopyranosyl-(1→4)-D-glucopyranosyl]urea are dissolved in a mixture of 150 ml of tetrahydrofuran and 20 ml of acetic acid, and 20 g of sodium acetate anhydrate are added thereto. 8 g of nitrogen tetroxide gas are introduced into the mixture for 10 minutes under ice-cooling and stirring. The mixture is further stirred at the same temperature for 20 minutes. 200 ml of n-hexane are added to the reaction mixture. Insoluble materials are removed by filtration. Then, the filtrate is condensed. 200 ml of a mixture of ether and methanol (40:1) are added to the residue, and the resultant oil is purified by silica gel chromatography (Solvent: ethyl acetate-chloroform-methanol (2:1:1)), whereby 2.9 g 1-(2-chloroethyl)-1-nitroso-3-(2-methoxyethyl)-3-[O-α-D-glucopyranosyl-(1→4)-D-glucopyranosyl]urea (i.e., 1-(2-chloroethyl)-1-nitroso-3-(2-methoxyethyl)-3-(D-maltosyl)urea) are obtained as pale yellow powder.

M.p. 52° C. (decomp.)
IR$\nu_{max}^{Nujol}$(cm$^{-1}$): 3350, 1695, 1070, 1025;
NMR(D$_2$O)δ: 3.38(s, OC$\underline{H}_3$):
$[\alpha]_D^{32}$ +54.2° (C=1.2, in methanol)

EXAMPLE 2

(1) 7.2 g of D-maltose monohydrate, 2.7 g of 3-methoxy-n-propylamine and 2.5 g of 2-chloroethyl isocyanate are treated in the same manner as descrived in Example 1-(1), whereby 9.0 g of 1-(2-chloroethyl)-3-(3-methoxy-n-propyl)-3-[O-α-D-glucopyranosyl-(1→4)-D-glucopyranosyl]urea (i.e., 1-(2-chloroethyl)-3-(3-methoxy-n-propyl)-3-(D-maltosyl)urea) are obtained as colorless powder.

IR$\nu_{max}^{Nujol}$(cm$^{-1}$): 3350, 1635, 1540, 1070, 1030
NMR(D$_2$O)δ: 1.75-2.15(m, 2H, —CH$_2$C$\underline{H}_2$CH$_2$—)
3.30(s, 3H, OC$\underline{H}_3$)

(2) 5.2 g of 1-(2-chloroethyl)-3-(3-methoxy-n-propyl)-3-[O-α-D-glucopyranosyl-(1→4)-D-glucopyranosyl]urea and 8 g of nitrogen tetroxide gas are treated in the same manner as described in Example 1-(2), whereby 3.0 g of 1-(2-chloroethyl)-1-nitroso-3-(3-methoxy-n-propyl)-3-[O-α-D-glucopyranosyl-(1→4)-D-glucopyranosyl]urea (i.e., 1-(2-chloroethyl)-1-nitroso-3-(3-methoxy-n-propyl)-3-(D-maltosyl)urea) are obtained as pale yellow powder.

M.p. 70°-74° C. (decomp.)
IR$\nu_{max}^{Nujol}$(cm$^{-1}$): 3350, 1700, 1070, 1030
NMR(D$_2$O)δ: 1.85-2.25(m, 2H, —CH$_2$C$\underline{H}_2$CH$_2$—);
3.30(s, 3H, OC$\underline{H}_3$).
$[\alpha]_D^{25}$ +62.4° (C=1.6, in methanol)

EXAMPLE 3

(1) 7.2 g of D-maltose monohydrate, 2.8 g of 2-ethoxyethylamine and 2.5 g of 2-chloroethyl isocyanate are treated in the same manner as described in Example 1-(1), whereby 8.9 g of 1-(2-chloroethyl)-3-(2-ethoxyethyl)-3-[O-α-D-glucopyranosyl-(1→4)-D-glucopyranosyl]urea (i.e., 1-(2-chloroethyl)-3-(2-ethoxyethyl)-3-(D-maltosyl)urea) are obtained as colorless powder.

IR$\nu_{max}^{Nujol}$(cm$^{-1}$): 3340, 1640, 1555, 1070, 1025
NMR(D$_2$O)δ: 1.20(t, OCH$_2$C$\underline{H}_3$)

(2) 5.2 g of 1-(2-chloroethyl)-3-(2-ethoxyethyl)-3-[O-α-D-glucopyranosyl-(1→4)-D-glucopyranosyl]urea and 8 g of nitrogen tetroxide gas are treated in the same manner as described in Example 1-(2), whereby 3.2 g of 1-(2-chloroethyl)-1-nitroso-3-(2-ethoxyethyl)-3-[O-α-D-glucopyranosyl-(1→4)-D-glucopyranosyl]urea (i.e., 1-(2-chloroethyl)-1-nitroso-3-(2-ethoxyethyl)-3-(D-maltosyl)urea) are obtained as pale yellow powder.

M.p. 58° C. (decomp.)

IR$\nu_{max}.^{Nujol}$(cm$^{-1}$): 3380, 1710, 1070, 1030

NMR(D$_2$O)δ: 1.21(t, OCH$_2$C$\underline{H}_3$)

$[\alpha]_D^{27}$ +52.0° (C=1.0, in methanol)

EXAMPLE 4

(1) 7.2 g of D-maltose monohydrate, 3.0 g of 3-ethoxy-n-propylamine and 2.5 g of 2-chloroethyl isocyanate are treated in the same manner as described in Example 1-(1), whereby 8.5 g of 1-(2-chloroethyl)-3-(3-ethoxy-n-propyl)-3-[O-α-D-glucopyranosyl-(1→4)-D-glucopyranosyl]urea (i.e., 1-(2-chloroethyl)-3-(3-ethoxy-n-propyl)-3-(D-maltosyl)urea) are obtained as colorless powder.

IR$\nu_{max}.^{Nujol}$(cm$^{-1}$): 3350, 1630, 1540, 1070, 1025

NMR(D$_2$O)δ: 1.20(t,3H, OCH$_2$C$\underline{H}_3$); 1.65-2.15(m, 2H, —CH$_2$C$\underline{H}_2$CH$_2$—).

(2) 5.3 g of 1-(2-chloroethyl)-3-(3-ethoxy-n-propyl)-3-[O-α-D-glucopyranosyl-(1→4)-D-glucopyranosyl]urea and 8 g of nitrogen tetroxide gas are treated in the same manner as described in Example 1-(2), whereby 3.0 g of 1-(2-chloroethyl)-1-nitroso-3-(3-ethoxy-n-propyl)-3-[O-α-D-glucopyranosyl-(1→4)-D-glucopyranosyl]urea (i.e., 1-(2-chloroethyl)-1-nitroso-3-(3-ethoxy-n-propyl)-3-(D-maltosyl)urea) are obtained as pale yellow powder.

M.p. 63° C. (decomp.)

IR$\nu_{max}.^{Nujol}$(cm$^{-1}$): 3350, 1695, 1070, 1020

NMR(D$_2$O)δ: 1.17(t, 3H, OCH$_2$C$\underline{H}_3$); 1.80-2.30(m, 2H, —CH$_2$C$\underline{H}_2$CH$_2$—).

$[\alpha]_D^{32}$ +63.2° (C=1.1, in methanol)

EXAMPLE 5

(1) 7.2 g of D-maltose monohydrate, 3.0 g of 2-methoxy-n-propylamine and 2.5 g of 2-chloroethyl isocyanate are treated in the same manner as described in Example 1-(1), whereby 8.1 g of 1-(2-chloroethyl)-3-(2-methoxy-n-propyl)-3-[O-α-D-glucopyranosyl-(1→4)-D-glucopyranosyl]urea (i.e., 1-(2-chloroethyl)-3-(2-methoxy-n-propyl)-3-(D-maltosyl)urea) are obtained as colorless powder.

IR$\nu_{max}.^{Nujol}$(cm$^{-1}$): 3380, 1640, 1550, 1070, 1030

NMR (D$_2$O)δ: 2.20(d, 3H, —CH(OCH$_3$)C$\underline{H}_3$); 3.42(s, 3H, OC$\underline{H}_3$).

(2) 5.2 g of 1-(2-chloroethyl)-3-(2-methoxy-n-propyl)-3-[O-α-D-glucopyranosyl-(1→4)-D-glucopyranosyl]urea and 8 g of nitrogen tetroxide gas are treated in the same manner as described in Example 1-(2), whereby 3.3 g of 1-(2-chloroethyl)-1-nitroso-3-(2-methoxy-n-propyl)-3-[O-α-D-glucopyranosyl-(1→4)-D-glucopyranosyl]urea (i.e., 1-(2-chloroethyl)-1-nitroso-3-(2-methoxy-n-propyl)-3-(D-maltosyl)urea) are obtained as pale yellow powder.

M.p. 51° C. (decomp.)

IR$\nu_{max}.^{Nujol}$(cm$^{-1}$): 3380, 1700, 1075, 1030

NMR(D$_2$O)δ: 2.20(d, 3H, —CH(OCH$_3$)C$\underline{H}_3$); 3.36(s, 3H, OC$\underline{H}_3$).

$[\alpha]_D^{28}$ +55.3° (C=1.1, in methanol)

EXAMPLE 6

(1) 7.2 g of D-maltose monohydrate, 3.6 g of (1-methyl-2-methoxy-ethyl)amine and 3.5 g of 2-chloroethyl isocyanate are treated in the same manner as described in Example 1-(1), whereby 8.5 g of 1-(2-chloroethyl)-3-(1-methyl-2-methoxy-ethyl)-3-[O-α-D-glucopyranosyl-(1→4)-D-glucopyranosyl]urea (i.e., 1-(2-chloroethyl)-3-(1-methyl-2-methoxy-ethyl)-3-(D-maltosyl)urea) are obtained as colorless powder.

IR$\nu_{max}.^{Nujol}$(cm$^{-1}$): 3350, 1630, 1530, 1065, 1020

(2) 5.2 g of 1-(2-chloroethyl)-3-(1-methyl-2-methoxy-ethyl)-3-[O-α-D-glucopyranosyl-(1→4)-D-glucopyranosyl]-urea and 8 g of nitrogen tetroxide gas are treated in the same manner as described in Example 1-(2). 2.2 g of 1-(2-chloroethyl)-1-nitroso-3-(1-methyl-2-methoxy-ethyl)-3-[O-α-D-glycopyranosyl-(1→4)-D-glycopyranosyl]urea (i.e., 1-(2-chloroethyl)-1-nitroso-3-(1-methyl-2-methoxy-ethyl)-3-(D-maltosyl)urea) are thereby obtained as pale yellow powder.

M.p. 69° C. (decomp.)

IR$\nu_{max}.^{Nujol}$(cm$^{-1}$): 3350, 1700, 1070

NMR(D$_2$O)δ: 1.40(d, 3H, >CH—C$\underline{H}_3$); 3.33(s, 3H, OC$\underline{H}_3$).

$[\alpha]_D^{21}$ +59.8° (C=1.7, in methanol)

EXAMPLE 7

(1) 7.2 g of D-maltose monohydrate, 3 g of 2,3-dimethoxy-n-propylamine [Said amine is prepared by condensing 2,3-dihydroxy-n-propylazide with methyl iodide and hydrogenating the resultant 2,3-dimethoxy-n-propylazide in the presence of palladium-carbon. Hydrochloride: M.p. 73°–74° C., Mass (m/e) 120 (M$^+$+1)] and 2.5 g of 2-chloroethyl isocyanate are treated in the same manner as described in Example 1-(1), whereby 5.8 g of 1-(2-chloroethyl)-3-(2,3-dimethoxy-n-propyl)-3-[O-α-D-glucopyranosyl-(1→4)-D-glycopyranosyl]urea (i.e., 1-(2-chloroethyl)-3-(2,3-dimethoxy-n-propyl)-3-(D-maltosyl)urea) are obtained as colorless powder.

IR$\nu_{max}.^{Nujol}$(cm$^{-1}$): 3350, 1640, 1550, 1080, 1030

NMR(D$_2$O)δ: 3.35(s, 3H, OC$\underline{H}_3$); 3.42(s, 3H, OC$\underline{H}_3$).

(2) 5.5 g of 1-(2-chloroethyl)-3-(2,3-dimethoxy-n-propyl)-3-[O-α-D-glucopyranosyl-(1→4)-D-glucopyranosyl]urea and 8 g of nitrogen tetroxide gas are treated in the same manner as described in Example 1-(2), whereby 2.8 g of 1-(2-chloroethyl)-1-nitroso-3-(2,3-dimethoxy-n-propyl)-3-[O-α-D-glycopyranosyl-(1→4)-D-glucopyranosyl]urea (i.e., 1-(2-chloroethyl)-1-nitroso-3-(2,3-dimethoxy-n-propyl)-3-(D-maltosyl)urea) are obtained as pale yellow powder.

M.p. 54° C. (decomp.)

IR$\nu_{max}.^{Nujol}$(cm$^{-1}$): 3350, 1700, 1070, 1020

NMR(D$_2$O)δ: 3.38(s, 3H, OC$\underline{H}_3$), 3.43(s, 3H, OC$\underline{H}_3$); 4.18(t, 2H, —N(NO)C$\underline{H}_2$CH$_2$Cl).

$[\alpha]_D^{26}$ +50.7° (C=1.1, in methanol)

EXAMPLE 8

(1) 7.2 g of D-maltose monohydrate, 3 g of 2-(methoxy-methoxy)ethylamine [Said amine is prepared by condensing 2-hydroxy-ethylazide with chloromethyl methyl ether and reducing the resultant 2-(methoxy-methoxy)ethylazide with lithium aluminium hydride. B.p. (30 mmHg) 56° C.] and 2.5 g of 2-chloroethyl isocyanate are treated in the same manner as described in Example 1-(1), whereby 6.8 g of 1-(2-chloroethyl)-3-[2-(methoxy-methoxy)ethyl]-3-[O-α-D-glucopyranosyl-(1→4)-D-glucopyranosyl]urea (i.e., 1-(2-chloroethyl)-3-[2-(methoxy-methoxy)ethyl]-3-(D-maltosyl)urea) are obtained as colorless powder.

IR$\nu_{max}.^{Nujol}$(cm$^{-1}$): 3350, 1640, 1545, 1070, 1030

NMR(D$_2$O)δ: 3.32 (s, OC$\underline{H}_3$)

(2) 5.3 g of 1-(2-chloroethyl)-3-(methoxy-methoxy)ethyl]-3-[O-α-D-glucopyranosyl-(1→4)-D-glucopyranosyl]-urea are dissolved in 200 ml of tetrahydrofuran, and 20 g of sodium carbonate anhydrate are added thereto. 8 g of nitrogen tetroxide gas are introduced into the mixture for 20 minutes under ice-cooling and stirring. The mixture is further stirred at the same temperature for 30 minutes. 200 ml of n-hexane are added to the reaction mixture, and said mixture is filtered. 10 ml of methanol are added to the filtrate, and the resultant oil is collected therefrom. Said oil is washed with ether and then purified by silica gel chromatography (Solvent: ethyl acetate - chloroform -methanol (2:1:1)), whereby 2.6 g of 1-(2-chloroethyl)-1-nitroso-3-[2-(methoxy-methoxy)ethyl]-3-[O-α-D-glucopyranosyl-(1→4)-D-glucopyranosyl]urea (i.e., 1-(2-chloroethyl)-1-nitroso-3-[2-(methoxy-methoxy)ethyl]-3-(D-maltosyl)urea) are obtaned as pale yellow powder.

M.p. 60° C. (decomp.)
IR$\nu_{max.}^{Nujol}$(cm$^{-1}$): 3360, 1710, 1070, 1025
NMR(d$_6$-DMSO)δ: 3.24(s, 3H, OC$\underline{H}_3$); 4.56(s, 2H, —O—C$\underline{H}_2$—O—).
$[\alpha]_D^{32}$ +49.2° (C=1.2, in methanol)

EXAMPLE 9

(1) A mixture of 7.2 g of D-maltose monohydrate, 3.2 g of diglycolamine and 15 ml of methanol are heated at 60° to 65° C. for one hour. Then, the precipitates are collected by filtration and washed with methanol, whereby 1-[2-(2-hydroxyethoxy)ethylamino]-1-deoxy-D-maltose is obtained. The product is dissolved in 20 ml of water, and 2.5 g of 2-chloroethyl isocyanate are added dropwise thereto at 0° to 5° C. under stirring. The mixture is stirred at the same temperature for 1.5 hours. Then, said mixture is condensed at 40° C. under reduced pressure to dryness. 10.2 g of 1-(2-chloroethyl)-3-[2-(2-hydroxyethoxy)ethyl]-3-[O-α-D-glucopyranosyl-(1→4)-D-glucopyranosyl]urea (i.e., 1-(2-chloroethyl)-3-[2-(2-hydroxyethoxy)ethyl]-3-(D-maltosyl)urea) are thereby obtained as colorless powder.

IR$\nu_{max.}^{Nujol}$(cm$^{-1}$): 3340, 1630, 1540, 1070, 1030

(2) 5.5 g of 1-(2-chloroethyl)-3-[2-(2-hydroxyethoxy)ethyl]-3-[O-α-D-glucopyranosyl-(1→4)-D-glucopyranosyl]-urea and 8.0 g of nitrogen tetroxide gas are treated in the same manner as described in Example 1-(2). 3.2 g of 1-(2-chloroethyl)-1-nitroso-3-[2-(2-hydroxyethoxy)ethyl]-3-[O-α-D-glucopyranosyl(1→4)-D-glucopyranosyl]urea (i.e., 1-(2-chloroethyl)-1-nitroso-3-[2-(2-hydroxyethoxy)ethyl]-3-(D-maltosyl)urea are thereby obtained as pale yellow powder.

M.p. 78° C. (decomp.)
IR$\nu_{max.}^{Nujol}$(cm$^{-1}$): 3350, 1695, 1060, 1030
$[\alpha]_D^{20}$ +53.6° (C=1.0, in methanol)

EXAMPLE 10

(1) A mixture of 3.8 g of D-ribose, 3.8 g of 2-methoxyethylamine and 5 ml of methanol is heated at 50° to 55° C. for 15 minutes under stirring. The reaction mixture is condensed to dryness under reduced pressure. The residue is washed with ether, whereby 1-(2-methoxyethylamino)-1-deoxy-D-ribose is obtained as a crude product. Said crude product is dissolved in 40 ml of methanol, and a solution of 3.5 g of 2-chloroetyl isocyanate in 10 ml of tetrahydrofuran is added dropwise thereto at 0° to 5° C. Said mixture is stirred at the same temperature for one hour. After the reaction, said mixture is condensed under reduced pressure. The residue thus obtained is washed with ether, whereby 7.0 g of 1-(2-chloroethyl)-3-(2-methoxyethyl)-3-(D-ribofuranosyl)urea are obtained as colorless caramel.

IR$\nu_{max.}^{neat}$(cm$^{-1}$): 3320, 1630, 1540, 1110
NMR(D$_2$O)δ: 3.40(s, OC$\underline{H}_3$)

(2) 3.1 g of 1-(2-chloroethyl)-3-(2-methoxyethyl)-3-(D-ribofuranosyl)urea are dissolved in a mixture of 60 ml of tetrahydrofuran and 60 ml of methylene chloride, and 15 g of sodium carbonate anhydrate are added thereto. 5 g of nitrogen tetroxide gas are introduced into the mixture for 10 minutes under ice-cooling and stirring. The mixture is stirred at the same temperature for 10 minutes. Then, 10 ml of methanol and 3 ml of water are added to the mixture, and said mixture is stirred vigorously at 0° to 5° C. for 10 minutes. The mixture is dried and filtered. The filtrate is condensed under reduced pressure. The residue obtained is purified by silica gel chromatography (Solvent: ethyl acetate-chloroform-methanol (5:2:1)), whereby 2.2 g of 1-(2-chloroethyl)-1-nitroso-3-(2-methoxyethyl)-3-(D-ribofuranosyl)urea are obtained as yellow oil.

IR$\nu_{max.}^{liquid}$(cm$^{-1}$): 3425, 1710, 1080, 1050, 1020
NMR(D$_2$O)δ: 3.36(s, 3H, OC$\underline{H}_3$); 4.24(t, 2H, —N(-NO)—C$\underline{H}_2$CH$_2$Cl).
$[\alpha]_D^{32}$ −21.9° (C=1.1, in methanol)

EXAMPLE 11

(1) 3.8 g of D-ribose, 4.0 g of 2-ethoxyethylamine and 3.5 g of 2-chloroethyl isocyanate are treated in the same manner as described in Example 10-(1), whereby 8.0 g of 1-(2-chloroethyl)-3-(2-ethoxyethyl)-3-(D-ribofuranosyl)urea are obtained as a brown oil.

IR$\nu_{max.}^{liq.}$(cm$^{-1}$): 3350, 1640, 1560, 1110
NMR(D$_2$O)δ: 1.20(t, OCH$_2$C$\underline{H}_3$)

(2) 3.3 g of 1-(2-chloroethyl)-3-(2-ethoxyethyl)-3-(D-ribofuranosyl)urea and 5 g of nitrogen tetroxide gas are treated in the same manner as described in Example 10-(2), whereby 2.7 g of 1-(2-chloroethyl)-1-nitroso-3-(2-ethoxyethyl)-3-(D-ribofuranosyl)urea are obtained as an yellow oil.

IR$\nu_{max.}^{liq.}$(cm$^{-1}$): 3420, 1700, 1110, 1080, 1050
NMR(D$_2$O)δ: 1.16(t, 3H, OCH$_2$C$\underline{H}_3$); 4.20(t, 2H, —N(NO)C$\underline{H}_2$—).
$[\alpha]_D^{22}$ −17.1° (C=2.5, in methanol)

EXAMPLE 12

(1) A mixture of 3.0 g of L-arabinose, 2.3 g of 2-methoxyethylamine and 10 ml of methanol is heated at 60° to 65° C. for 20 minutes under stirring. The reaction mixture is condensed to dryness under reduced pressure. The residue is washed with ether, whereby 1-(2-methoxyethylamino)-1-deoxy-L-arabinose is obtained as a crude product. Said crude product is dissolved in 40 ml of methanol, and a solution of 2.5 g of 2-chloroethyl isocyanate in 10 ml of tetrahydrofuran is added dropwise thereto at 0° to 5° C. Said mixture is stirred at the same temperature for one hour. After the reaction, the mixture is condensed under reduced pressure. The residue obtained is dissolved in 20 ml of formic acid, said solution is allowed to stand at room temperature for 15 minutes, and 150 ml of a mixture of ether and hexane (3:1) are added thereto. The resultant oil is washed with ether, whereby 5.5 g of 1-(2-chloroethyl)-3-(2-methoxyethyl)-3-(L-arabinopyranosyl)urea are obtained as pale light brown caramel.

IR$\nu_{max.}^{Nujol}$(cm$^{-1}$): 3350, 1640, 1540, 1090
NMR(D$_2$O)δ: 3.35(s, 3H, OC$\underline{H}_3$) 4.90(d, 1H, C$_1$—H)

(2) 3.1 g of 1-(2-chloroethyl)-3-(2-methoxyethyl)-3-(L-arabinopyranosyl)urea and 5 g of nitrogen tetroxide gas are treated in the same manner as described in Example 10-(2), whereby 2.4 g of 1-(2-chloroethyl)-1-nitroso-3-(2-methoxyethyl)-3-(L-arabinopyranosyl)urea are obtained as yellow caramel.

IRν$_{max.}$$^{CHCl3}$(cm$^{-1}$): 3420, 1695, 1080

NMR(D$_2$O)δ: 3.35(s, 3H, OCH$_3$) 4.20(t, 2H, —N(-NO)—; CH$_2$CH$_2$Cl) 4.90(d, 1H, C$_1$—H).

[α]$_D$$^{25}$ +45.5° (C=1.5, in methanol)

EXAMPLE 13

(1) A mixture of 3.0 g of L-arabinose, 3.6 g of 3-methoxy-n-propylamine and 10 ml of methanol is heated at 60° to 65° C. for 20 minutes under stirring. The reaction mixture is condensed to dryness under reduced pressure, and the residue is washed with ether. 4.3 g of 1-(3-methoxy-n-propylamino)-1-deoxy-L-arabinose are obtained as a crude product. Said crude product are dissolved in 40 ml of methanol, and a solution of 3.0 g of 2-chloroethyl isocyanate in 10 ml of tetrahydrofuran is added dropwise thereto at 0° to 5° C. Said mixture is stirred at the same temperature for one hour. After the reaction, the mixture is condensed under reduced pressure. The residue obtained is dessolved in 20 ml of formic acid, and the solution is allowed to stand at room temperature for 15 minutes. 150 ml of a mixture of ether and n-hexane (3:1) are added to the solution. The resultant oil is collected by decantation and then purified by silica gel chromatography (Solvent: ethyl acetate-chloroform-methanol (2:1:1)), whereby 5.3 g of 1-(2-chloroethyl)-3-(3-methoxy-n-propyl)-3-(L-arabinopyranosyl)urea are obtained as colorless caramel.

IRν$_{max.}$$^{CHCl3}$(cm$^{-1}$): 3370, 1640, 1530, 1090

NMR(D$_2$O)δ: 1.6–2.1 (m, 2H, —CH$_2$CH$_2$CH$_2$OCH$_3$); 3.35(s, 3H, OCH$_3$); 4.90(d, 1H, C$_1$—H).

(2) 3.3 g of 1-(2-chloroethyl)-3-(3-methoxy-n-propyl)-3-(L-arabinopyranosyl)urea and 5 g of nitrogen tetroxide gas are treated in the same manner as described in Example 10-(2), whereby 2.2 g of 1-(2-chloroethyl)-1-nitroso-3-(3-methoxy-n-propyl)-3-(L-arabinopyranosyl)urea are obtained as pale yellow powder.

M.p. 100°–101° C. (decomp.)

IRν$_{max.}$$^{Nujol}$(cm$^{-1}$): 3400, 1700, 1075

NMR(D$_2$O)δ: 1.75–2.20(m, 2H, —CH$_2$CH$_2$CH$_2$OCH$_3$); 3.35(s, 3H, OCH$_3$); 4.10(t, 2H, —N(NO)CH$_2$—); 4.90(d, 1H, C$_1$—H).

[α]$_D$$^{22}$+50.0° (C=1.6, in methanol)

EXAMPLE 14

(1) 3.0 g of L-arabinose, 3.6 g of 2-methoxy-n-propylamine and 3.5 g of 2-chloroethyl isocyanate are treated in the same manner as described in Example 13-(1). 3.0 g of 1-(2-chloroethyl)-3-(2-methoxy-n-propyl)-3-(L-arabinopyranosyl)urea are thereby obtained as colorless caramel.

IRν$_{max.}$$^{Nujol}$(cm$^{-1}$): 3350, 1640, 1545, 1080, 1055, 1000

NMR(D$_2$O)δ: 1.15(d, 3H, >CH—CH$_3$); 3.38(s, 3H, OCH$_3$).

(2) 3.3 g of 1-(2-chloroethyl)-3-(2-methoxy-n-propyl)-3-(L-arabinopyranosyl)urea and 5 g of nitrogen tetroxide gas are treated in the same manner as described in Example 10-(2). 2.5 g of 1-(2-chloroethyl)-1-nitroso-3-(2-methoxy-n-propyl)-3-(L-arabinopyranosyl)urea are thereby obtained as yellow powder.

M.p. 60° C.(decomp.)

IRν$_{max.}$$^{Nujol}$(cm$^{-1}$): 3400, 1695, 1080, 1050, 1020

NMR(D$_2$O)δ: 1.20(d, 3H, >CH—CH$_3$); 3.34(s, 3H, OCH$_3$).

[α]$_D$$^{22}$+30.5° (C=0.9, in methanol)

EXAMPLE 15

(1) 3.0 g of L-arabinose, 3.6 g of (1-methyl-2-methoxy-ethyl)amine and 3.5 g of 2-chloroethyl isocyanate are treated in the same manner as described in Example 13-(1). 3.1 g of 1-(2-chloroethyl)-3-(1-methyl-2-methoxy-ethyl)-3-(L-arabinopyranosyl)urea are thereby obtained as colorless caramel.

IRν$_{max.}$$^{Nujol}$(cm$^{-1}$): 3320, 1630, 1520, 1080

(2) 3.3 g of 1-(2-chloroethyl)-3-(1-methyl-2-methoxy-ethyl)-3-(L-arabinopyranosyl)urea and 5 g of nitrogen tetroxide gas are treated in the same manner as described in Example 10-(2). 1.0 g of 1-(2-chloroethyl)-1-nitroso-3-(1-methyl-2-methoxy-ethyl)-3-(L-arabinopyranosyl)urea are thereby obtained as yellow caramel.

IRν$_{max.}$$^{CHCl3}$(cm$^{-1}$): 3400, 1700, 1080

NMR(D$_2$O)δ: 1.40(d, 3H, >CH—CH$_3$); 3.30(s, 3H, OCH$_3$).

[α]$_D$$^{22}$+42.6° (C=1.5, in methanol)

EXAMPLE 16

(1) 3.0 g of D-arabinose, 3.6 g of 3-methoxy-n-propylamine and 3.0 g of 2-chloroethyl isocyanate are treated in the same manner as described in Example 13-(1). 5.0 g of 1-(2-chloroethyl)-3-(3-methoxy-n-propyl)-3-(D-arabinopyranosyl)-urea are thereby obtained as colorless caramel.

IRν$_{max.}$$^{CHCl3}$(cm$^{-1}$): 3370, 1640, 1530, 1085

NMR(D$_2$O)δ: 1.6–2.1(m, 2H, —CH$_2$CH$_2$CH$_2$OCH$_3$); 3.35(s, 3H, OCH$_3$); 4.90(d, 1H, C$_1$—H).

(2) 3.3 g of 1-(2-chloroethyl)-3-(3-methoxy-n-propyl)-3-(D-arabinopyranosyl)urea and 5 g of nitrogen tetroxide gas are treated in the same manner as described in Example 10-(2). 2.0 g of 1-(2-chloroethyl)-1-nitroso-3-(3-methoxy-n-propyl)-3-(D-arabinopyranosyl)urea are thereby obtained as pale yellow powder.

M.p. 102°–103° C.(decomp.)

IRν$_{max.}$$^{Nujol}$(cm$^{-1}$): 3400, 1700, 1075

NMR(D$_2$O+d$_6$-DMSO)δ: 1.75–2.20(m, 2H, —CH$_2$CH$_2$CH$_2$OCH$_3$); 3.33(s, 3H, OCH$_3$); 4.16(t, 2H, —N(NO)CH$_2$—); 4.83(d, 1H, C$_1$—H).

[α]$_D$$^{22}$−50.1° (C=1.4, in methanol)

EXAMPLE 17

(1) 3.8 g of D-xylose, 3.8 g of 2-methoxyethylamine and 3.5 g of 2-chloroethyl isocyanate are treated in the same manner as described in Example 13-(1), whereby 6.1 g of 1-(2-chloroethyl)-3-(2-methoxyethyl)-3-(D-xylopyranosyl)urea are obtained as colorless caramel.

IRν$_{max.}$$^{Nujol}$(cm$^{-1}$): 3350, 1640, 1540, 1110, 1040

NMR(D$_2$O)δ: 3.35(s, 3H, OCH$_3$), 5.0(d, 1H, C$_1$—H)

(2) 3.1 g of 1-(2-chloroethyl)-3-(2-methoxyethyl)-3-(D-xylopyranosyl)urea and 5 g of nitrogen tetroxide gas are treated in the same manner as described in Example 10-(2), whereby 2.5 g of 1-(2-chloroethyl)-1-nitroso-3-(2-methoxyethyl)-3-(D-xylopyranosyl)urea are obtained as yellow caramel.

IRν$_{max.}$$^{CHCl3}$(cm$^{-1}$): 3410, 1695, 1105, 1080

NMR(CDCl$_3$)δ: 3.35(s, OCH$_3$)

[α]$_D$$^{28}$+4.9° (C=1.2, in methanol)

EXAMPLE 18

(1) 3.6 g of D-mannose, 2.6 g of 2-methoxyethylamine and 2.5 g of 2-chloroethyl isocyanate are treated in the same manner as described in Example 10-(1), whereby 6.5 g of 1-(2-chloroethyl)-3-(2-methoxyethyl)-3-(D-mannopyranosyl)urea are obtained as colorless caramel.

IRν$_{max}$.$^{Nujol}$(cm$^{-1}$): 3320, 1630, 1550, 1110, 1060

NMR(D$_2$O)δ: 3.40(s, OCH$_3$)

(2) 3.4 g of 1-(2-chloroethyl)-3-(2-methoxyethyl)-3-(D-mannopyranosyl)urea are dissolved in a mixture of 40 ml of tetrahydrofuran and 10 ml of acetic acid, and 17 g of sodium acetate anhydrate are added thereto. 6 g of nitrogen tetroxide gas are introduced into the mixture for 10 minutes under ice-cooling and stirring. The mixture is further stirred at the same temperature for 10 minutes. 70 ml of hexane are added to the reaction mixture, and said mixture is filtered. The filtrate is condensed under reduced pressure. A mixture of 200 ml of hexane and 4 ml of methanol is added to the residue. After the resultant oil is washed with ether, said oil is dissolved in 50 ml of ethyl acetate. 10 ml of water are added to the ethyl acetate solution, and the mixture is shaken. Then, the ethyl acetate layer is collected therefrom, dried and evaporated under reduced pressure. 1.7 g of 1-(2-chloroethyl)-1-nitroso-3-(2-methoxyethyl)-3-(D-mannopyranosyl)urea is thereby obtained as pale yellow caramel.

IRν$_{max}$.$^{CHCl3}$(cm$^{-1}$): 3370, 1695, 1090, 1070

NMR(D$_2$O)δ: 3.30(s, OCH$_3$)

$[α]_D^{27}$+20.0° (C=1.5, in methanol)

EXAMPLE 19

(1) 3.6 g of D-galactose, 1.8 g of 2-methoxyethylamine and 2.5 g of 2-chloroethyl isocyanate are treated in the same manner as described in Example 12-(1), whereby 6.5 g of 1-(2-chloroethyl)-3-(2-methoxyethyl)-3-(D-galactopyranosyl)urea are obtained as pale light brown caramel.

IRν$_{max}$.$^{Nujol}$(cm$^{-1}$): 3350, 1630, 1545, 1110, 1060

NMR(D$_2$O)δ: 3.35(s, OCH$_3$)

(2) 3.4 g of 1-(2-chloroethyl)-3-(2-methoxyethyl)-3-(D-galactopyranosyl)urea and 5 g of nitrogen tetroxide gas are treated in the same manner as described in Example 10-(2), whereby 2.7 g of 1-(2-chloroethyl)-1-nitroso-3-(2-methoxyethyl)-3-(D-galactopyranosyl)urea are obtained as pale yellow caramel.

IRν$_{max}$.$^{CHCl3}$(cm$^{-1}$): 3350, 1700, 1080

NMR(d$_6$-DMSO-D$_2$O)δ: 3.26(s, 3H, OCH$_3$) 4.82(d, 1H, C$_1$—H).

$[α]_D^{20}$+9.2° (C=1.1, in methanol)

EXAMPLE 20

(1) 3.6 g of D-galactose, 2.5 g of 3-methoxy-n-propylamine and 2.5 g of 2-chloroethyl isocyanate are treated in the same manner as described in Example 13-(1), whereby 5.1 g of 1-(2-chloroethyl)-3-(3-methoxy-n-propyl)-3-(D-galactopyranosyl)urea are obtained as colorless caramel.

IRν$_{max}$.$^{Nujol}$(cm$^{-1}$): 3330, 1630, 1540, 1050

NMR(D$_2$O)δ: 1.75–2.15(m, 2H, —CH$_2$CH$_2$CH$_2$—); 3.35(s, 3H, OCH$_3$).

(2) 3.6 g of 1-(2-chloroethyl)-3-(3-methoxy-n-propyl)-3-(D-galactopyranosyl)urea and 5 g of nitrogen tetroxide gas are treated in the same manner as described in Example 10-(2), whereby 2.8 g of 1-(2-chloroethyl)-1-nitroso-3-(3-methoxy-n-propyl)-3-(D-galactopyranosyl)urea are obtained as pale yellow caramel.

IRν$_{max}$.$^{CHCl3}$(cm$^{-1}$): 3380, 1700, 1080

NMR(D$_2$O)δ: 1.80–2.25(m, 2H, —CH$_2$CH$_2$CH$_2$—) 3.35(s, 3H, OCH$_3$); 4.20(t, 2H, —N(NO)—CH$_2$CH$_2$Cl).

$[α]_D^{20}$+15.5° (C=1.3, in methanol)

EXAMPLE 21

(1) 3.6 g of D-galactose, 3.5 g of (1-methyl-2-methoxy-ethyl)amine and 3.5 g of 2-chloroethyl isocyanate are treated in the same manner as described in Example 13-(1). 3.8 g of 1-(2-chloroethyl)-3-(1-methyl-2-methoxy-ethyl)-3-(D-galactopyranosyl)urea are thereby obtained as colorless caramel.

IRν$_{max}$.$^{Nujol}$(cm$^{-1}$): 3360, 1635, 1540, 1080, 1040

(2) 3.6 g of 1-(2-chloroethyl)-3-(1-methyl-2-methoxy-ethyl)-3-(D-galactopyranosyl)urea and 5 g of nitrogen tetroxide gas are treated in the same manner as described in Example 10-(2). 1.3 g of 1-(2-chloroethyl)-1-nitroso-3-(1-methyl-2-methoxy-ethyl)-3-(D-galactopyranosyl)urea are thereby obtained as yellow powder.

M.p. 56° C.(decomp.)

IRν$_{max}$.$^{Nujol}$(cm$^{-1}$): 3400, 1690, 1090, 1040

NMR(D$_2$O)δ: 1.38(d, 3H, >CH—CH$_3$); 3.33(s, 3H, OCH$_3$).

$[α]_D^{21}$+12.9° (C=1.0, in methanol)

EXAMPLE 22

(1) 3.6 g of D-galactose, 3.5 g of 2,2-diethoxyethylamine and 2.5 g of 2-chloroethyl isocyanate are treated in the same manner as described in Example 10-(1), whereby 7.2 g of 1-(2-chloroethyl)-3-(2,2-diethoxyethyl)-3-(D-galactopyranosyl)urea are obtained as colorless caramel.

IRν$_{max}$.$^{Nujol}$(cm$^{-1}$): 3370, 1635, 1545, 1110, 1070

NMR(D$_2$O)δ: 1.06(t, OCH$_2$CH$_3$)

(2) 4.0 g of 2-(2-chloroethyl)-3-(2,2-diethoxyethyl)-3-(D-galactopyranosyl)urea and 5 g of nitrogen tetroxide gas are treated in the same manner as described in Example 10-(2), whereby. 1.5 g of 1-(2-chloroethyl)-1-nitroso-3-(2,2-diethoxyethyl)-3-(D-galactopyranosyl)urea is obtained as pale yellow caramel.

IRν$_{max}$.$^{CHCl3}$(cm$^{-1}$): 3400, 1700, 1120, 1070

NMR(d$_6$-DMSO)δ: 1.08(t, 6H, OCH$_2$CH$_3$); 4.80(d, 1H, C$_1$—H).

$[α]_D^{20}$−3.4° (C=1.4, in methanol)

EXAMPLE 23

(1) 3.6 g of D-glucose, 2.7 g of 3-methoxy-n-propylamine and 3.0 g of 2-chloroethyl isocyanate are treated in the same manner as described in Example 13-(1), whereby 6.5 g of 1-(2-chloroethyl)-3-(3-methoxy-n-propyl)-3-(D-glucopyranosyl)-urea are obtained as colorless caramel.

IRν$_{max}$.$^{Nujol}$(cm$^{-1}$): 3350, 1640, 1530, 1110, 1070, 1020

NMR(D$_2$O)δ: 1.70–2.20(m, 2H, —CH$_2$CH$_2$CH$_2$—); 3.30(s, 3H, OCH$_3$); 5.00(d, 1H, C$_1$—H).

(2) 3.6 g of 1-(2-chloroethyl)-3-(3-methoxy-n-propyl)-3-(D-glucopyranosyl)urea and 5 g of nitrogen tetroxide gas are treated in the same manner as described in Example 10-(2), whereby 2.7 g of 1-(2-chloroethyl)-1-nitroso-3-(3-methoxy-n-propyl)-3-(D-glucopyranosyl)urea are obtained as yellow caramel.

IRν$_{max}$.$^{CHCl3}$(cm$^{-1}$): 3400, 1695, 1070

NMR(D$_2$O)δ: 1.75–2.30(m, 2H, —CH$_2$CH$_2$CH$_2$—); 3.35(s, 3H, OCH$_3$); 4.20(t, 2H, —N(NO)—CH$_2$CH$_2$Cl); 5.0(d, 1H, C$_1$—H).

$[α]_D^{28}$+9.8° (C=1.2, in methanol)

EXAMPLE 24

3.3 g of 1-(2-chloroethyl)-3-(3-methoxy-n-propyl)-3-(L-arabinopyranosyl)urea are dissolved in 15 ml of formic acid, and 1.5 g of sodium nitrite are added gradually thereto at 0° C. for one hour under stirring. The mixture is further stirred at the same temperature for one hour. After the reaction, 15 ml of ethanol are added to the reaction mixture. Said mixture is neutralized with potassium carbonate under ice-cooling. Then, 150 ml of ethyl acetate are added to said mixture and insoluble materials are removed by filtration. The filtrate is washed with an aqueous sodium bicarbonate solution, dried and evaporated to remove solvent. The residue thus obtained is purified by silica gel chromatography (Solvent: ethyl acetate-chloroform-methanol=5:2:1). 1.2 g of 1-(2-chloroethyl)-1-nitroso-3-(3-methoxy-n-propyl)-3-(L-arabinopyranosyl)urea are thereby obtained as yellow caramel.

$[\alpha]_D^{22} + 50.0°$ (C=1.5, in methanol)

EXAMPLE 25

3.6 g of 1-(2-chloroethyl)-3-(1-methyl-2-methoxy-ethyl)-3-(D-galactopyranosyl)urea and 1.5 g of sodium nitrite are treated in the same manner as described in Example 24. 0.9 g of 1-(2-chloroethyl)-1-nitroso-3-(1-methyl-2-methoxy-ethyl)-3-(D-galactopyranosyl)urea are thereby obtained as yellow powder.

$[\alpha]_D^{21} + 12.9°$ (C=1.0, in methanol)

What is claimed is:

1. A compound of the formula:

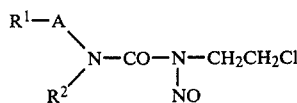

wherein $R^1$ is lower alkoxy, lower alkoxy-methoxy or 2-hydroxyethoxy, $R^2$ is aldo-pentofuranosyl, aldo-pentopyranosyl, aldo-hexopyranosyl or O-aldo-hexopyranosyl-(1→4)-aldo-hexopyranosyl, and A is straight or branched alkylene of one to four carbon atoms, said alkylene being substituted with from 0 to at least one lower alkoxy group.

2. The compound of claim 1, in which $R^2$ is D-ribofuranosyl, L-arabinopyranosyl, D-arabinopyranosyl, D-xylopyranosyl, D-glucopyranosyl, D-galactopyranosyl, D-mannopyranosyl or O-α-D-glucopyranosyl-(1→4)-D-glucopyranosyl.

3. The compound of claim 2, in which $R^1$ is alkoxy of one or two carbon atoms.

4. The compound of claim 3, in which A is straight or branched alkylene of two or three carbon atoms.

5. The compound of claim 4, in which $R^2$ is D-ribofuranosyl, L-arabinopyranosyl, D-arabinopyranosyl, D-xylopyranosyl, D-galactopyranosyl, D-mannopyranosyl or O-α-D-glucopyranosyl-(1→4)-D-glucopyranosyl.

6. The compound of claim 4, in which $R^2$ is L-arabinopyranosyl, D-arabinopyranosyl or O-α-D-glucopyranosyl-(1→4)-D-glucopyranosyl, and A is ethylene, propylene, 1-methylethylene or 2-methylethylene.

7. The compound of claims 5 or 6, in which A is ethylene or propylene.

8. The compound of claims 5 or 6, in which A is 1-methylethylene or 2-methylethylene.

9. The compound of claim 6, in which $R^1$ is methoxy.

10. The compound of claim 9, in which A is ethylene or propylene.

11. The compound of claim 9, in which A is 1-methylethylene or 2-methylethylene.

12. The compound of claim 10 which is 1-(2-chloroethyl)-1-nitroso-3-(2-methoxyethyl)-3-(L-arabinopyranosyl)urea.

13. The compound of claim 10 which is 1-(2-chloroethyl)-1-nitroso-3-(3-methoxy-n-propyl)-3-(L-arabinopyranosyl)urea.

14. The compound of claim 10 which is 1-(2-chloroethyl)-1-nitroso-3-(3-methoxy-n-propyl)-3-(D-arabinopyranosyl)-urea.

15. The compound of claim 11 which is 1-(2-chloroethyl)-1-nitroso-3-(2-methoxy-n-propyl)-3-[O-α-D-glucopyranosyl-(1→4)-D-glucopyranosyl]urea.

16. The compound of claim 11 which is 1-(2-chloroethyl)-1-nitroso-3-(1-methyl-2-methoxy-ethyl)-3-[O-α-D-glucopyranosyl-(1→4)-D-glucopyranosyl]urea.

17. The compound of claim 11 which is 1-(2-chloroethyl)-1-nitroso-3-(2-methoxy-n-propyl)-3-(L-arabinopyranosyl)-urea.

18. The compound of claim 11 which is 1-(2-chloroethyl)-1-nitroso-3-(1-methyl-2-methoxy-ethyl)-3-(L-arabinopyranosyl)urea.

19. A compound of the forumula:

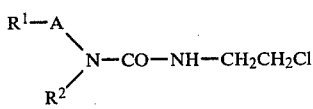

wherein $R^1$ is lower alkoxy, lower alkoxy-methoxy or 2-hydroxyethoxy, $R^2$ is aldo-pentofuranosyl, aldo-pentopyranosyl, aldo-hexopyranosyl or O-aldo-hexopyranosyl(1→4)-aldo-hexopyranosyl, and A is straight or branched alkylene of one to four carbon atoms, said alkylene being substituted with from 0 to at least one lower alkoxy group.

20. A therapeutic composition which comprises a therapeutically effective amount of a compound of claim 1 and a pharmaceutically acceptable carrier.

* * * * *